(12) United States Patent
Niermann et al.

(10) Patent No.: US 6,602,206 B1
(45) Date of Patent: Aug. 5, 2003

(54) STOPPER-SHIELD ASSEMBLY

(75) Inventors: Volker Niermann, Little Falls, NJ (US); Michael J. Iskra, Bridgewater, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/640,238

(22) Filed: Aug. 16, 2000

Related U.S. Application Data

(60) Provisional application No. 60/149,580, filed on Aug. 18, 1999.

(51) Int. Cl.[7] ................................................ A61B 5/00
(52) U.S. Cl. ...................................................... 600/573
(58) Field of Search ................................ 600/573, 574, 600/575, 576, 577, 578, 579, 580; 215/200; 604/317

(56) References Cited

U.S. PATENT DOCUMENTS

| | | | | |
|---|---|---|---|---|
| 4,441,951 A | | 4/1984 | Christinger | 156/245 |
| 4,741,446 A | * | 5/1988 | Miller | 215/247 |
| 4,967,919 A | | 11/1990 | Earhart | 215/247 |
| 5,060,659 A | | 10/1991 | Cook et al. | 128/764 |
| 5,361,921 A | | 11/1994 | Burns | 215/320 |
| 5,779,074 A | * | 7/1998 | Burns | 215/247 |
| 2001/0020607 A1 | | 9/2001 | Chiarin | 215/247 |

* cited by examiner

*Primary Examiner*—Max F. Hindenburg
*Assistant Examiner*—Pamela L. Wingood
(74) *Attorney, Agent, or Firm*—Nanette S. Thomas, Esq.; Scott J. Rittman, Esq.

(57) ABSTRACT

The present invention is a stopper and shield closure assembly 16 millimeter (mm) fluid collection tube whereby the 16 millimeter tube is compatible with conventional needle holders.

1 Claim, 9 Drawing Sheets

STOPPER-SHIELD ASSEMBLY

This application claims benefit of provisional application 60/149,580 filed Aug. 18, 1999.

BACKGROUND OF THE INVENTION

1. Field of the Invention

The present invention relates to a stopper and shield closure for fluid collection tubes and more particularly to a stopper and shield closure assembly for 16 millimeters (mm) fluid collection tubes.

2. Description of Related Art

An evacuated blood collection tube is commonly used by a doctor, phlebotomist or nurse to draw a sample of body fluids from a patient in a hospital or doctor's office for diagnostic testing. During the use of such a tube, a double-ended needle that is attached to a needle holder, is inserted in a vein of the patient, and the closure end of the evacuated tube is inserted into the open end of the holder until the needle in the holder pierces the tube's closure. The blood collection tube contains a vacuum that then draws a body fluid sample from the patient into the tube. Therefore, it is important for the closure on the tube to fit securely on the open end of the tube and maintain the vacuum in the tube before, during and after the blood collection procedure.

Currently, closures for 13 millimeter or less evacuated blood collection tubes may include plastic shields containing a rubber stopper, wherein the stopper is thick or has an enlarged head to fit snugly within and remain attached to the shield and a plug portion that fits in the open end of the tube. Retention of the stopper in the shield is important when the shield and stopper are being removed from the open end of the tube so that blood within the tube can be tested and when the tube is mated with the end of a double ended needle in a needle holder and body fluid is being obtained from a patient.

Standard needle holders, have a fixed internal diameter and accept 13 millimeter or less evacuated blood collection tubes that have a plastic shield containing a rubber stopper. Standard needle holders will also accept 16 millimeter evacuated blood collection tubes that have a rubber stopper and not a plastic shield. Standard needle holders are not compatible with 16 millimeter evacuated blood collection tubes that have a plastic shield that is scaled up from a 13 millimeter tube because the outside diameter of the plastic shield is greater than the internal diameter of the standard needle holder.

Therefore, there exists a need to provide a stopper and shield closure on a 16 millimeter tube that is compatible with standard needle holders.

SUMMARY OF THE INVENTION

The present invention is a specific stopper-shield assembly comprising a plastic shield that is mounted over a rubber stopper for use with a 16 millimeter evacuated tube and that would be compatible with standard needle holders.

The present invention provides a stopper and shield closure assembly having an overall diameter the same or similar to that of stopper and shield closure used with 13 millimeter tubes.

Most preferably, the stopper-shield assembly of the present invention comprises dimensions whereby use of the stopper-shield assembly with a 16 millimeter plastic tube may be used with a conventional needle holder. The dimensions of the stopper-shield assembly have been minimized to be compatible with conventional needle holders while maintaining the aspects, features and advantages of a stopper-shield assembly that is currently used with 13 millimeter plastic tubes.

Most preferably, the two-piece composite closure of the present invention is for use with 16 millimeter plastic tubes. The two-piece composite closure preferably comprises a plastic shield and a rubber stopper.

Most notably is that the two-piece composite closure of the present invention comprises an outside diameter that is not proportional to the scale up of the stopper and shield closure assembly that is used with a 13 millimeter tube.

An important feature of the stopper and shield closure assembly of the present invention is that the diameter of the assembly allows the closure to fit in conventional needle holders.

Another important feature is that the shield material is more rigid than shields commonly used with tubes of 13 millimeters or less.

A further notable advantage is that the two-piece composite provides a 16 millimeter tube with a closure that can be used with conventional needle holders.

DETAILED DESCRIPTION

Figures 1, 2:
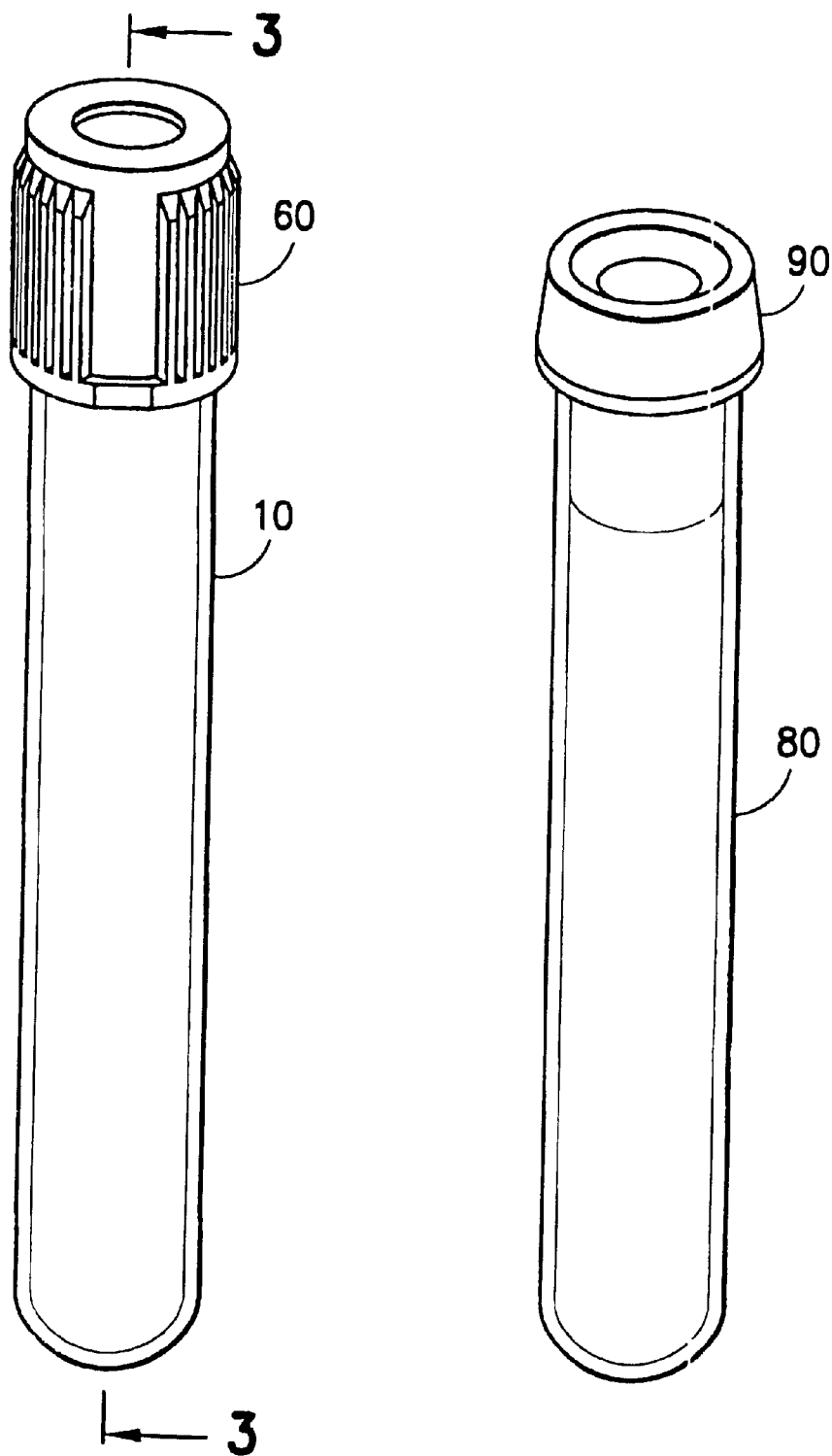
FIG. 1 (prior art) perspective view of a 13 millimeter assembly.
FIG. 2 (prior art) perspective view of a 16 millimeter assembly.

Referring to the drawings in which like reference characters refer to like parts throughout the several views thereof, FIGS. 1, 3, 4 and 5, illustrate a standard 13 millimeter tube 10 with a stopper 40 and a shield 60 and FIG. 2 illustrates a standard 16 millimeter tube 80 with a stopper 90.

Figure 3:
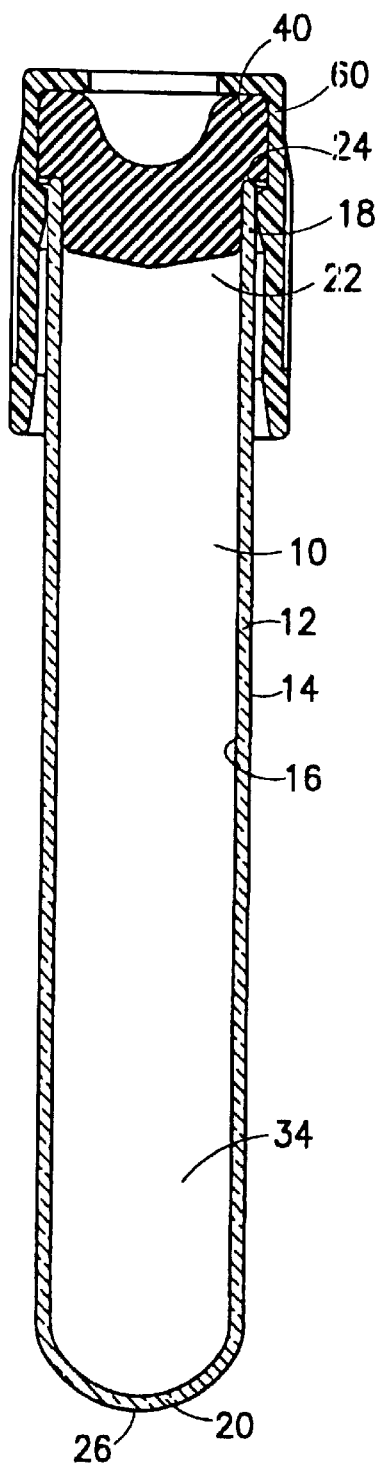
FIG. 3 (prior art) cross sectional view of the container and closure of FIG. 1 taken along 3—3 thereof.
Figure 4:
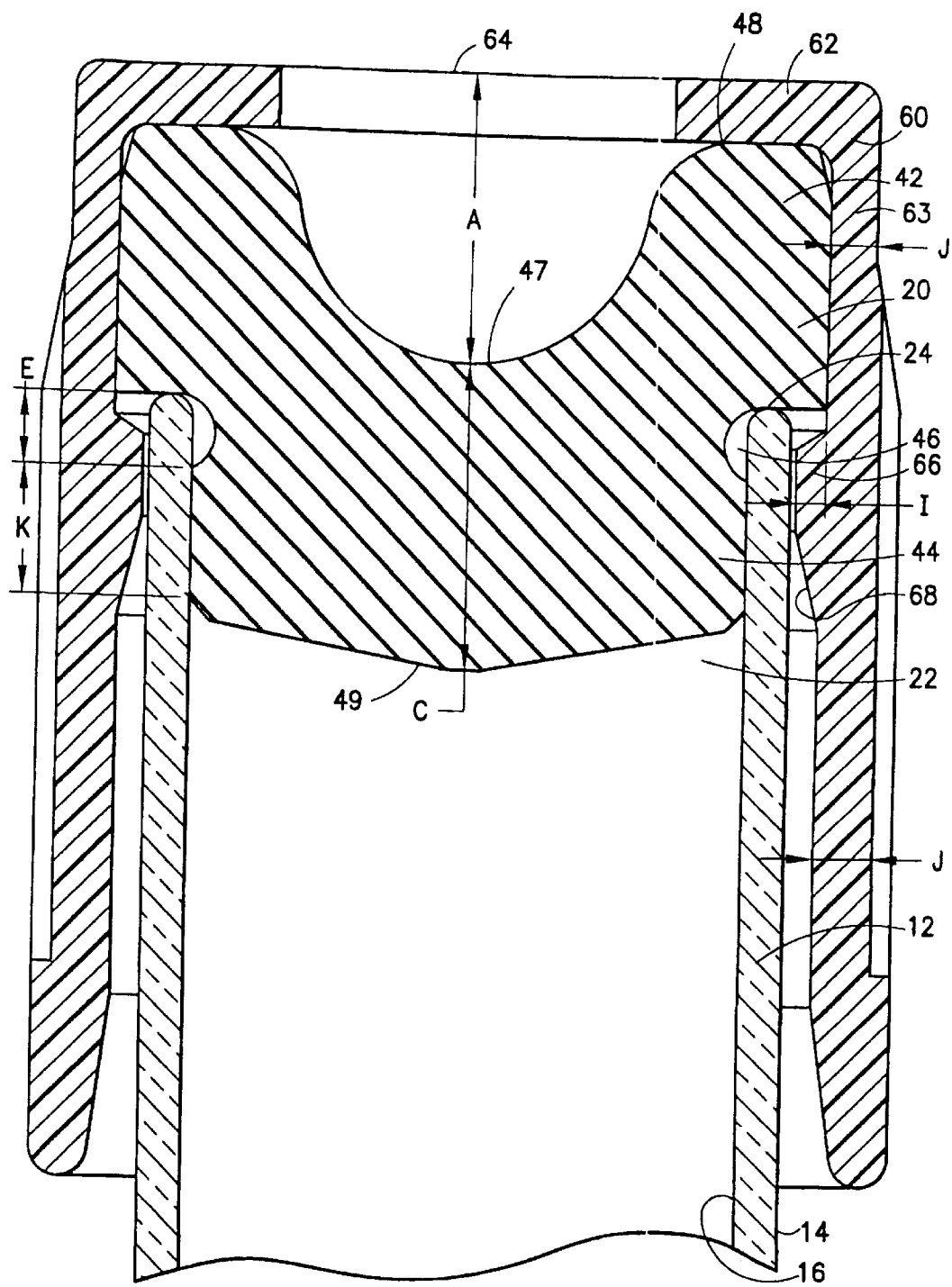
FIG. 4 (prior art) enlarged cross-sectional view of the assembly of FIG. 3.

As shown in FIGS. 3 and 4, tube 10 comprises a sidewall 12 having an outer surface 14 and an inner surface 16. Sidewall 12 extends from an upper portion 18 to a lower portion 20. Upper portion 18 includes an open end 22 and a rim 24. Lower portion 20 comprises a closed bottom end 26. Interior volume 34 extends between top surface 24 and closed bottom end 26.

As shown in FIG. 4, stopper 20 has a radially enlarged upper flange portion 42 and a smaller lower sealing portion 44. Positioned between upper portion 42 and lower portion 44 is a radial notch 46. Positioned centrally in the top surface 48 of stopper 20 is a finger well 47. The bottom surface 49 of stopper 20 is convex.

Extending over the top of stopper 20 is a plastic cap or shield 60 which may be comprised of a flexible thermoplastic resin and which includes a radially extending top 62 for extending over the top surface 48 of stopper 20 and an annular skirt 63 extending from top 62. Radially extending top surface defines an opening 64 through which a needle may pass to be inserted into and through stopper 20. An integral annular abutment 66 is provided to engage the stopper. Annular abutment 66 includes a tapered surface for ease of assembly of cap 60 over upper flange 42 of stopper 20.

Figure 5:
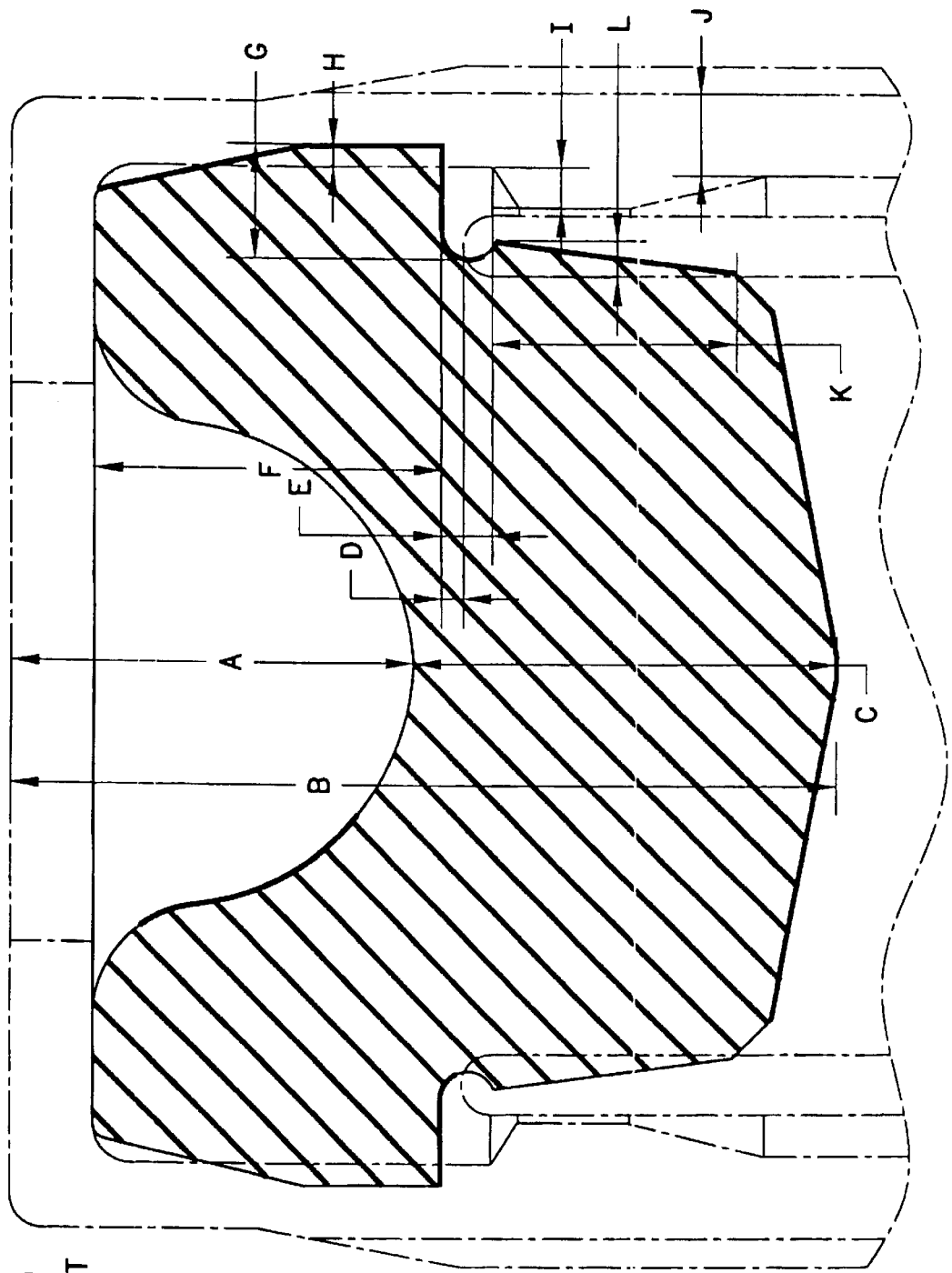
FIG. 5 (prior art) enlarged cross-sectional view of the assembly of FIG. 3.

The dimensions of stopper 20 and cap 60 are illustrated in FIG. 5 and are as follows:

TABLE 1

| DIMENSION | INCHES |
| --- | --- |
| A | .217 |
| B | .442 |
| C | .225 |
| D | .013 |
| E | .028 |
| F | .215 |
| G | .061 |
| H | .018 |
| I | .019 |
| J | .041 |
| K | .126 |
| L | .021 |

Figure 6:
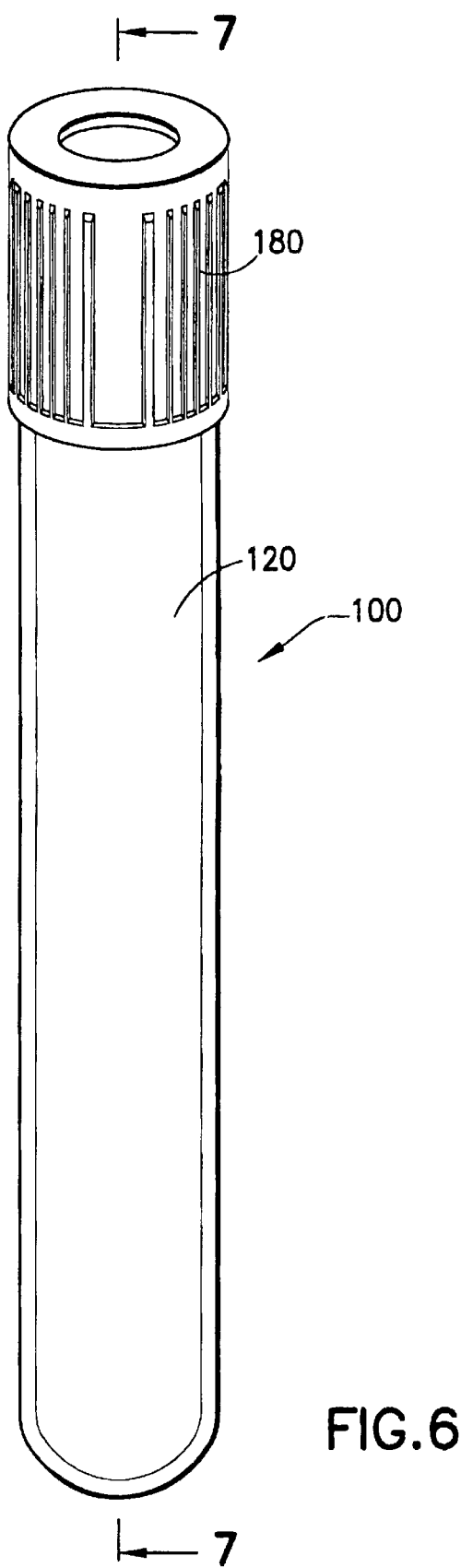
FIG. 6 is a perspective view of the assembly of the present invention illustrating the container with the closure.
Figures 7, 8:
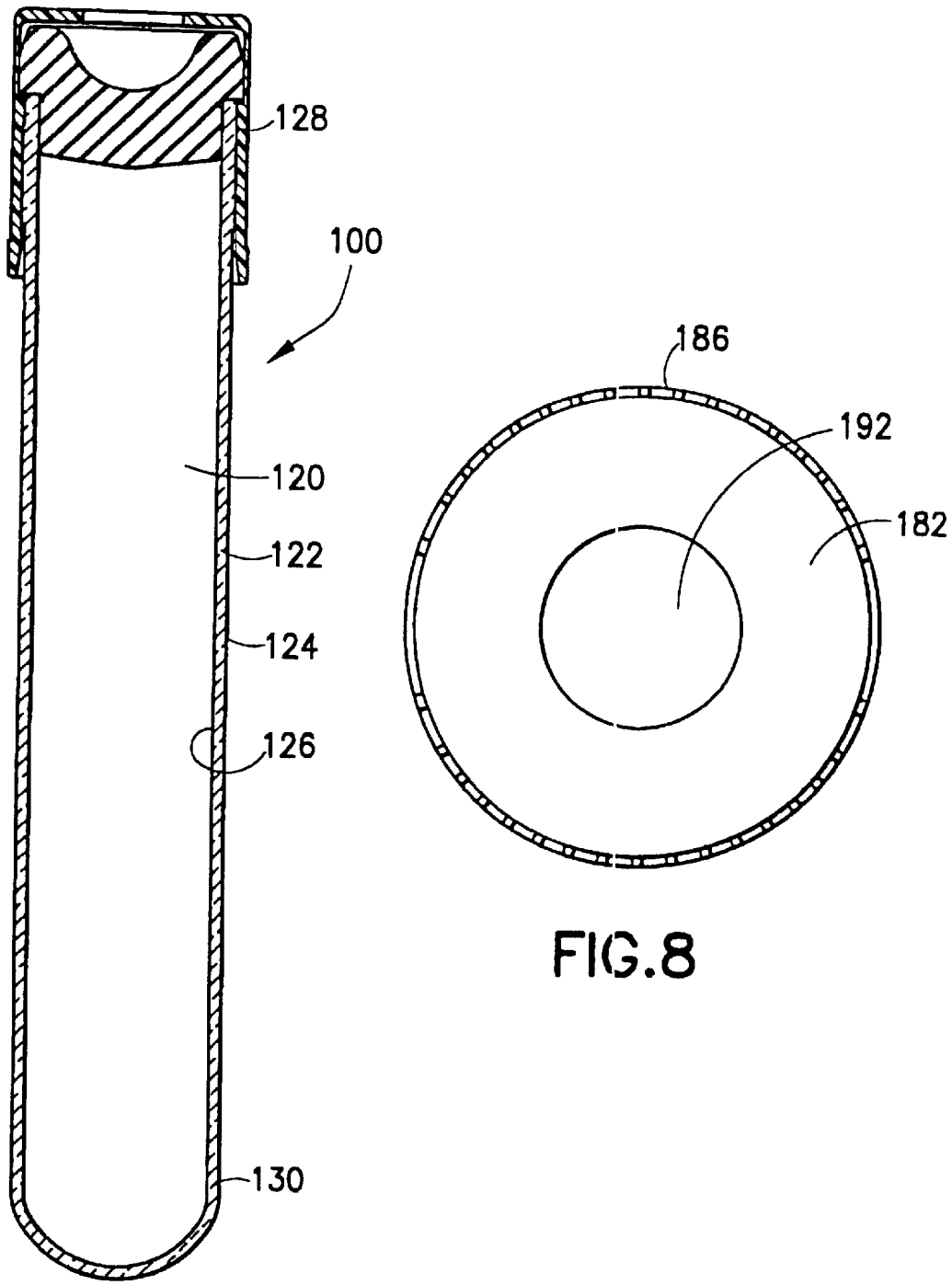
FIG. 7 is a cross sectional view of the assembly of the present invention of FIG. 6 taken along line 7—7 thereof.
FIG. 8 is a t op view of the closure of FIG. 6.
Figure 9:
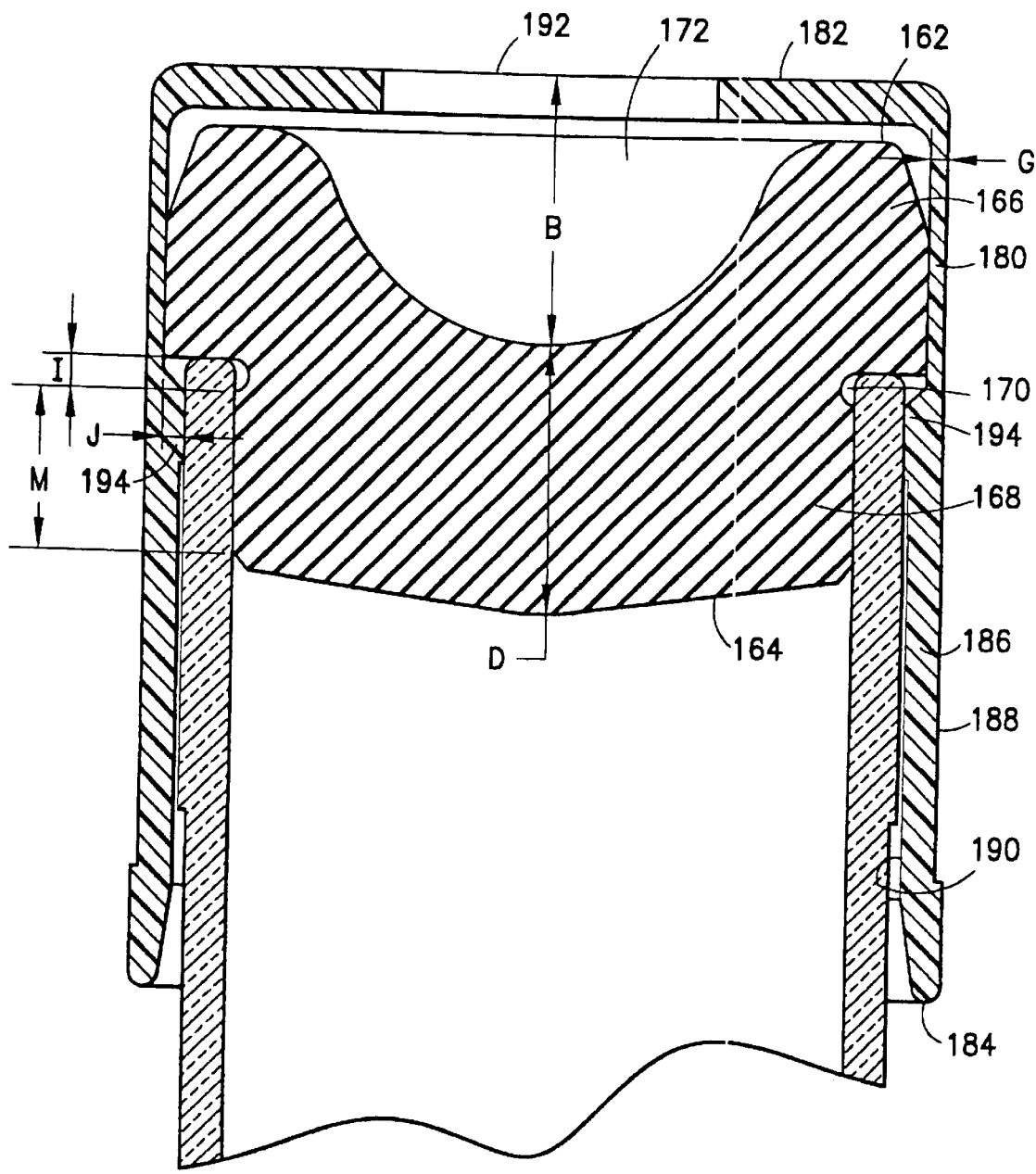
FIG. 9 is an enlarged cross sectional view of the assembly of FIG. 7.

FIGS. 6 and 7, illustrate the 16 millimeter tube assembly 100 of the present invention. The assembly comprises a tube 120, a stopper 160 and a shield 180.

As shown in FIGS. 6, 7, 8 and 9 assembly 100 of the present invention comprises a tube 120 that comprises a sidewall 122 having an outer surface 124 and an inner surface 126 and extending from an upper portion 128 to a lower portion 130.

Stopper 160 includes a top surface 162, a bottom surface 164, a radially enlarged upper flange portion 166 and a smaller lower annular sealing portion 168. Positioned between upper portion 166 and lower portion 168 is a radial notch 170. Upper portion 166 defines a top surface 162 wherein a finger well 172 is positioned centrally. The bottom surface 174 of stopper 160 is convex. Although it is within the purview of the invention that bottom surface 174 of stopper 160 is concave.

Extending over the top of stopper 160 is a plastic cap or shield 180 which may be comprised of a flexible thermoplastic resin and which includes a top surface 182, a bottom stop ledge 184, an annular outer skirt 186 extending from the top surface to the bottom stop ledge. Annular outer skirt 186 has an outer wall surface 188 and inner wall surface 190. Shield 180 further includes a central opening 192 in top surface 182. An integral annual abutment 194 is provided to engage the tube. Annular abutment includes a tapered surface for ease of assembly of shield 180 over upper flange 166 of stopper 160.

Figure 10:
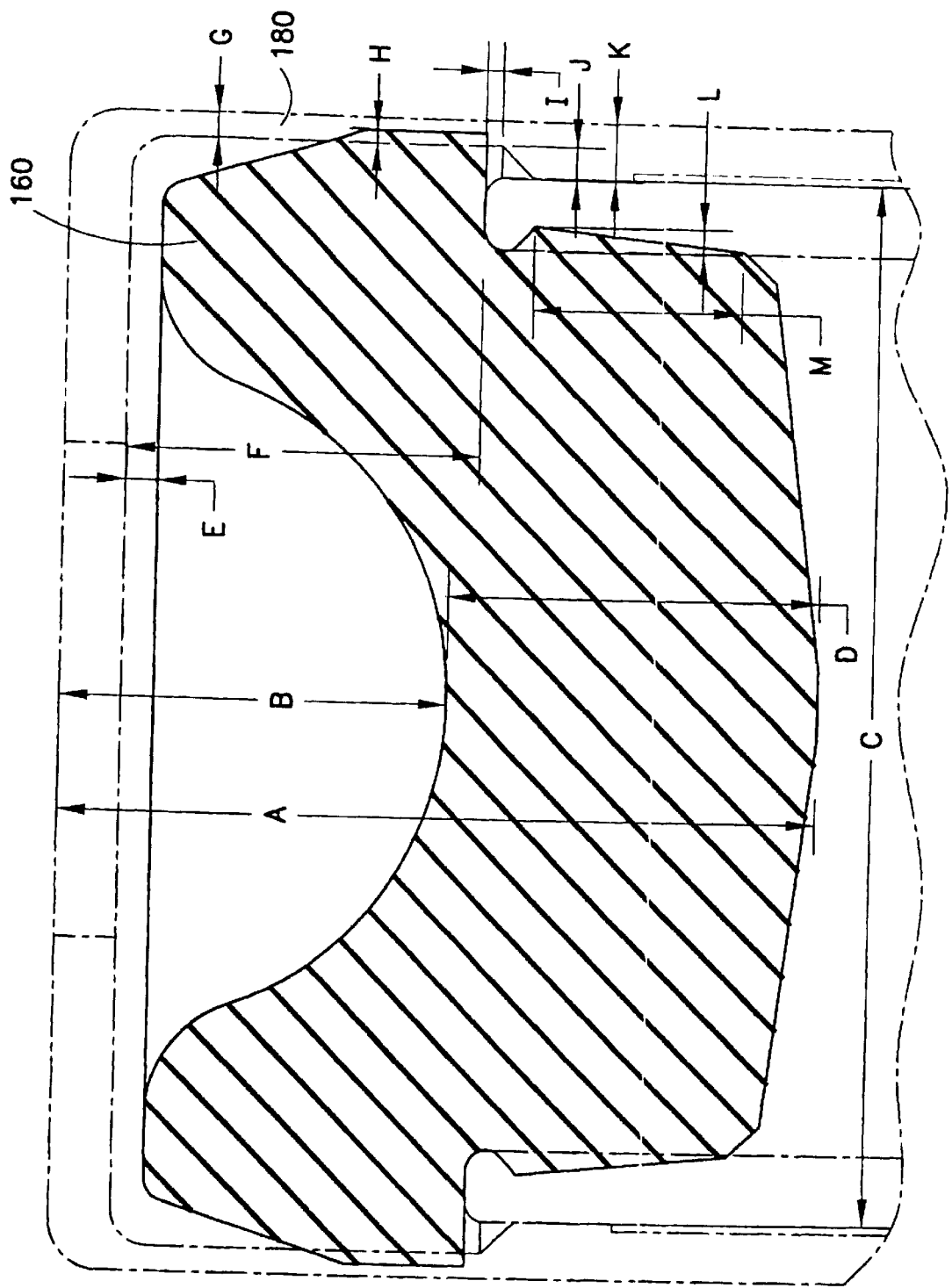
FIG. 10 is an enlarged cross sectional view of the assembly of FIG. 7.

The dimensions of stopper 160 and shield 180 are illustrated in FIG. 10 measured with reference to said center-line A axis and are as follows:

TABLE 2

| DIMENSION | INCHES |
| --- | --- |
| A | .462 |
| B | .235 |
| C | .615 |
| D | .227 |
| E | .018 |
| F | .225 |
| G | .015 |
| H | .013 |
| I | .010 |
| J | .016 |
| K | .032 |
| L | .016 |
| M | .129 |

Most notably is that the dimension H of annular outer skirt 186 of shield 180 is 0.011 to 0.021 and most preferably 0.013, the dimension J of annular abutment 194 of shield 180 is 0.008 to 0.018 and most preferably 0.016, and dimension D of stopper 168 is 0.227 so that a 16 millimeter tube may be used with a conventional needle holder.

Figure 11:
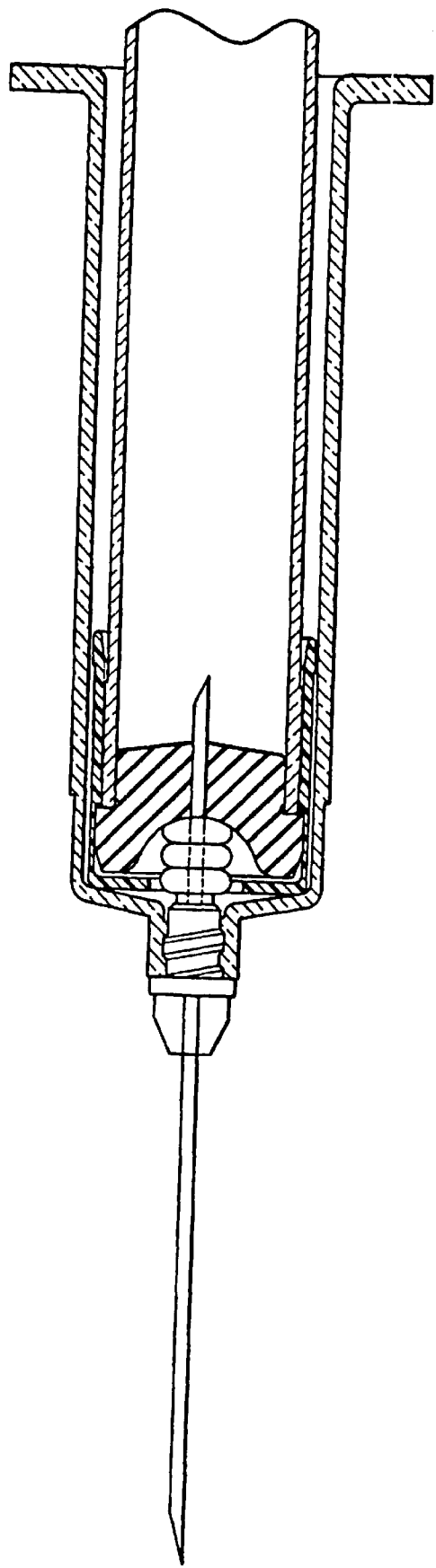
FIG. 11 is a cross sectional view of the assembly of the present invention shown in FIG. 7 mounted in a conventional needle holder.

Therefore as shown in FIG. 11, the 16 millimeter tube assembly of the present invention of FIG. 7, which includes a stopper and a shield, is compatible with a standard needle holder.

What is claimed:

1. A closure assembly for sealing an open end of a body fluid collection tube comprising:

a stopper comprising an annular stopper body with an integral upper flange portion; a lower integral annular sealing portion on said body; an annular notch in said body at the interface of said upper flange portion and said lower sealing portion; wherein the outer annular surface of said lower portion being the sealing surface with a container and tapered inwardly continuously toward the axis of said body, said taper being from said annular notch to the bottom surface of said lower annular sealing portion; said bottom surface of said annular sealing portion being convex; and a flexible cap body for mounting on said stopper comprising a top surface, a bottom stop ledge, an annular skirt extending from said top surface to said bottom stop ledge; said annular skirt comprising an outer wall surface and an inner wall surface; a central opening in said top surface; an integral annular abutment on said inner wall surface with a tapered surface;

wherein said integral annular abutment having a width of 0.011 to 0.021 inches and said annular skirt having a width of 0.008 to 0.018 inches with respect to said center-line axis.

* * * * *

UNITED STATES PATENT AND TRADEMARK OFFICE
CERTIFICATE OF CORRECTION

PATENT NO. : 6,602,206 B1
APPLICATION NO. : 09/640238
DATED : August 5, 2003
INVENTOR(S) : Volker Niermann et al.

It is certified that error appears in the above-identified patent and that said Letters Patent is hereby corrected as shown below:

Claim 1, Col. 4, lines 21-58; should read:

A closure assembly for sealing an open end of a body fluid collection tube comprising:

a stopper comprising an annular stopper body with an integral upper flange portion; a lower integral annular sealing portion on said body; an annular notch in said body at the interface of said upper flange portion and said lower sealing portion; wherein the outer annular surface of said lower portion being the sealing surface with a container and tapered inwardly continuously toward the axis of said body, said taper being from said annular notch to the bottom surface of said lower annular sealing portion; said bottom surface of said annular sealing portion being convex; and a flexible cap body for mounting on said stopper comprising a top surface, a bottom stop ledge, an annular skirt extending from said top surface to said bottom stop ledge; said annular skirt comprising an outer wall surface and an inner wall surface; a central opening in said top surface; an integral annular abutment on said inner wall surface with a tapered surface;

wherein said integral annular abutment having a width of 0.008 to 0.018 inches and said annular skirt having a width of 0.011 to 0.021 inches with respect to said center-line axis.

Signed and Sealed this

Twenty-fifth Day of November, 2008

JON W. DUDAS
*Director of the United States Patent and Trademark Office*